United States Patent [19]

Walser

[11] 4,352,814
[45] Oct. 5, 1982

[54] TREATMENT OF HEPATIC AND RENAL DISORDERS WITH MIXED SALTS OF ESSENTIAL OR SEMI-ESSENTIAL AMINO ACIDS AND NITROGEN-FREE ANALOGS

[75] Inventor: Mackenzie Walser, Ruxton, Md.

[73] Assignee: The Johns Hopkins University, Baltimore, Md.

[21] Appl. No.: 300,336

[22] Filed: Sep. 8, 1981

Related U.S. Application Data

[62] Division of Ser. No. 31,274, Apr. 18, 1979, Pat. No. 4,296,127.

[51] Int. Cl.³ ................. A61K 31/195; A61K 31/415
[52] U.S. Cl. ............................... 424/273 R; 424/317; 424/319
[58] Field of Search ................... 424/319, 317, 273 R; 562/444, 445, 456, 457, 459, 460, 461, 462, 470, 475

[56] References Cited

U.S. PATENT DOCUMENTS

| | | | |
|---|---|---|---|
| 2,457,820 | 1/1949 | Howe et al. | 424/319 |
| 3,441,650 | 4/1969 | Georges et al. | 424/316 |
| 3,764,703 | 10/1973 | Bergstrom et al. | 424/319 |

OTHER PUBLICATIONS

Richards et al., Lancet, pp. 845–849 (1967).
Reidman, J. Clinical Invest., vol. 50, pp. 90–96 (1971).
Walser, Chem. Abst., vol. 81, #54452q (1974).
Sapir et al., J. Clinical Invest., vol. 54, pp. 974–980 (1974).

Primary Examiner—Natalie Trousof
Assistant Examiner—James H. Reamer
Attorney, Agent, or Firm—Seidel, Gonda, Goldhammer & Panitch

[57] ABSTRACT

Novel compounds are prepared by reacting essential or semi-essential amino acids with nitrogen-free analogues thereof, particularly alpha-keto and/or alpha-hydroxy analogues. The mixed salt reaction products are precursors of essential and semi-essential amino acids in the body, and mixtures of the salts are useful in the treatment of renal and hepatic disorders characterized by protein intolerance leading to deficiencies of various essential and semi-essential amino acids in the body. They may also be useful in the treatment of nitrogen wasting disorders and protein malnutrition. The novel compounds are generally far more palatable and soluble in aqueous solutions than the individual essential or semi-essential amino acids, nitrogen-free analogues thereof, or simple mixtures of these.

6 Claims, 1 Drawing Figure

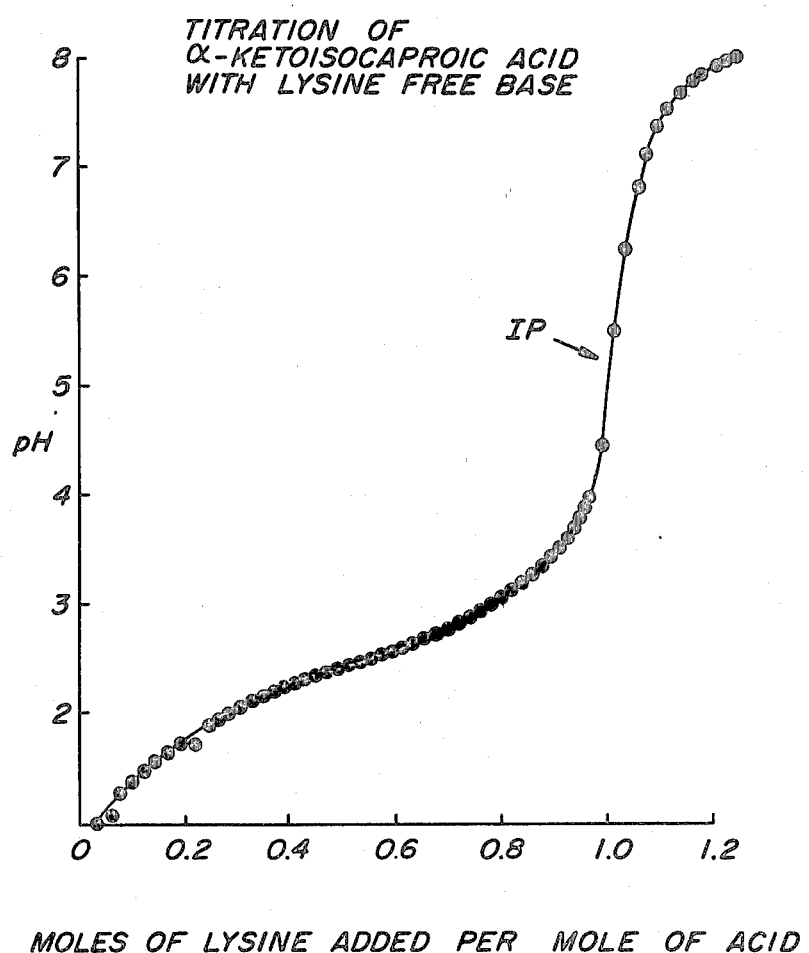

TREATMENT OF HEPATIC AND RENAL DISORDERS WITH MIXED SALTS OF ESSENTIAL OR SEMI-ESSENTIAL AMINO ACIDS AND NITROGEN-FREE ANALOGS

STATEMENT OF GOVERNMENT INTEREST

The invention described herein was made in part in the course of work under a grant or award from the United States Department of Health, Education and Welfare, National Institutes of Health.

This application is a division of my co-pending application Ser. No. 031,274 filed Apr. 18, 1979 now U.S. Pat. No. 4,296,127, for "MIXED SALTS OF ESSENTIAL OR SEMI-ESSENTIAL AMINO ACIDS, ETC."

BACKGROUND OF THE INVENTION

The present invention is directed to mixed salts of essential or semi-essential amino acids and nitrogen-free analogues thereof, and to the use of these novel salts in the treatment of renal and hepatic disorders. More particularly, the invention is directed to the novel compounds per se, compositions containing mixtures of the novel compounds, and methods of treatment using the compounds.

The essential amino acids in man are L-isoleucine, L-leucine, L-valine, L-methionine, L-phenylalanine, L-histidine, L-lysine, L-tryptophan and L-threonine. The semi-essential amino acids for man include L-tyrosine, L-cystine, and L-cysteine, which are believed to be required for optimal growth in infants. Arginine is essential in children who have defects of one of the enzymes of the urea cycle, but is not generally considered essential or semi-essential in normal man, although it may have nutritional value. Ornithine is also not generally considered essential or semi-essential in man, but will substitute for arginine. Nevertheless, for ease of reference in the present disclosure arginine and ornithine will be grouped with and referred to as semi-essential amino acids, unless otherwise indicated.

Renal disorders (such as uremia), hepatic diseases (such as hyperammonemia and portal-systemic encephalopathy), and other protein or nitrogen wasting diseases of man result in severe deficiencies of essential and/or semi-essential amino acids which are needed for building protein in the body. Thus, individuals suffering from renal and hepatic disorders must either be restricted in their ingestion of dietary protein due to the inability of the kidneys to excrete nitrogenous wastes, or they are intolerant of dietary protein due to the vomiting, agitation, lethargy and impaired mental and physical processes which occur following protein ingestion.

Prior art treatment of these protein or nitrogen wasting disorders has included the administration of certain essential amino acids to correct the protein deficiency, such as disclosed in U.S. Pat. No. 2,457,820 to Howe et al. Similarly, Bergstrom et al. in U.S. Pat. No. 3,764,703 disclose the use of a mixture of eight essential amino acids optionally combined with either or both L-arginine and L-histidine, which the patent terms "semi-essential" amino acids, for the treatment of uremic conditions caused by renal insufficiency.

More recently, the treatment of these disorders has been improved by the use of mixtures of nitrogen-free analogues of the essential amino acids, namely alpha-keto and alpha-hydroxy analogues of most of the essential amino acids, together with the essential amino acids per se whose analogues are not available or effective. Examples of such mixtures and treatments are described and claimed in my U.S. Pat. Nos. 4,100,160; 4,100,161 and 4,100,293, issued July 11, 1978. Another treatment of these disorders is disclosed in my U.S. Pat. No. 4,228,099, issued Oct. 14, 1980 entitled "Ornithine And Arginine Salts Of Branched Chain Keto Acids And Uses In Treatment Of Hepatic And Renal Disorders".

A significant obstacle to the use of essential amino acids per se or mixtures of nitrogen-free analogues of essential amino acids in the treatment of these nitrogen or protein wasting disorders is the unpleasant taste of these compounds. Thus, almost all of the essential amino acids per se and all of the keto analogues (as the free acids) are offensive and unpalatable. The calcium and sodium salts of the analogues are not quite as unpleasant as the essential amino acids per se, but can hardly be described as palatable, and therefore present a limitation on the oral use of these compounds for therapeutic purposes. The only oral product presently marketed in this country and containing exclusively essential amino acids is a product marketed by McGaw Laboratories under the trademark "AMINAID", which has a most unpleasant taste. The unpleasant taste can be masked by coating or tableting of the essential amino acids or analogues thereof, but this still leads to complaints of a bad aftertaste.

Another significant obstacle to the use of essential amino acids per se is their limited solubility in water such that they cannot generally be administered parenterally in a concentrated solution. For example, the only commercial product presently on the U.S. market containing solely essential amino acids for injection is a product marketed by McGaw Laboratories under the trademark "NEPHRAMINE". This 5.1 percent aqueous solution of eight essential amino acids (excluding histidine) is very near the limit of solubility at 0° C. The volume of water which must be administered limits the use of this product, especially in severe renal failure.

Although lysine and threonine are very soluble as such, tyrosine and cystine are very insoluble per se. For this reason, the inclusion of tyrosine or cystine in solutions for parenteral administration to infants has been impossible. Cysteine is quite soluble but becomes spontaneously oxidized to its dimer (cystine) in neutral or alkaline solution or on exposure to air. The remaining essential and semi-essential amino acids have variably low solubility.

The acid salts of neutral amino acids, such as the hydrochloride salts, are very soluble. However, the hydrochloride salts are also quite acidic in solution, and since they do not exist above about pH 2, they are never used. The basic amino acids, on the other hand, are often used as the hydrochlorides, because they are less acidic and exist at physiological pH.

The alpha-keto acid analogues and alpha-hydroxy acid analogues are mostly water-miscible liquids, with the exception of the analogues of tryptophan, phenylalanine and tyrosine, which are solids with limited water solubility. The sodium salts of all of the analogues are soluble, but the use of sodium salts is often precluded by the sodium load entailed, which may be detrimental in patients with liver disease or kidney disease in particular. The calcium salts of the analogues are rather insoluble.

A variety of rather cumbersome techniques has been devised or proposed to circumvent these solubility problems. For example, linking tyrosine to another amino acid such as alanine in a peptide bond does solve the solubility problem, but is a very expensive way to go. The keto or hydroxy analogues of tyrosine would presumably be effective, and are somewhat soluble, but they are also very expensive to produce.

BRIEF SUMMARY OF THE INVENTION

The above problems of the prior art are alleviated by the novel compounds of the present invention which comprise the reaction product of an essential or semi-essential amino acid with a nitrogen-free analogue of an essential or semi-essential amino acid. The novel mixed salt compounds are formed in aqueous medium followed by removal of the water to yield a dry powder product. The compounds are tasteless or pleasant tasting, and in most, but not all, cases there is a substantial increase in the water solubility of the compounds as compared to the least soluble of the amino acid and nitrogen-free analogue which are reacted to form the compound.

As is the case with the alpha-keto and alpha-hydroxy analogues per se of the essential amino acids, the compounds of the present invention are effective as precursors which are converted by the body to essential and semi-essential amino acids, which may be utilized by the body for protein synthesis. Hence, mixtures of the compounds of the present invention are useful in the treatment of renal and hepatic disorders, and other nitrogen or protein wasting diseases characterized by deficiencies of some or all of the essential or semi-essential amino acids in the body.

DETAILED DESCRIPTION OF PREFERRED EMBODIMENTS

The novel compounds of the present invention are salts formed by the reaction of an essential or semi-essential amino acid with a nitrogen-free analogue of an essential or semi-essential amino acid, particularly an alpha-keto or alpha-hydroxy analogue of the amino acid. The compounds may be represented simply by the following empirical formula:

$$AN \cdot xH_2O$$

wherein A is selected from the group consisting of essential amino acids and semi-essential amino acids, N is selected from the group consisting of alpha-keto and alpha-hydroxy analogues of essential or semi-essential amino acids, and x may be 0 or a positive number which need not be an integer. Thus, x may represent water of hydration or free or bound water due to incomplete drying of the reaction product, in cases where it is not possible to obtain a completely anhydrous product. As hypothesized below each compound may exist as an equilibrium mixture of a mixed salt with its corresponding carbinolamine and Schiff base.

The nine essential amino acids and five semi-essential amino acids are listed in Table I, followed in most cases by their corresponding alpha-keto and alpha-hydroxy analogues. In some cases, the nitrogen-free analogues are known or believed to be ineffective as precursors of the corresponding essential amino acid in the body, and that has been indicated in Table I, where appropriate, rather than listing the name of the analogue. The analogues of arginine and ornithine are not nitrogen-free and tend to cyclize so that they are probably ineffective as amino acid precursors.

The essential amino acids and semi-essential amino acids per se are readily available commercially, and methods of synthesizing them are also known in the art. In the case of the basic amino acids, namely L-lysine, L-histidine, L-arginine and L-ornithine, the essential amino acids are used in the form of their free bases. In the case of the neutral amino acids, which include the remaining essential amino acids and three semi-essential amino acids, they are used in the form of the respective free amino acids.

Most of the nitrogen-free analogues of essential and semi-essential amino acids are also commercially available, generally as the calcium or sodium salts thereof. Methods of making the nitrogen-free analogues are also known in the art. The free acids of the analogues may be prepared from the salts thereof by addition of excess hydrochloric acid and subsequent extraction with ether and evaporation.

Each of the essential amino acids and semi-essential amino acids may be combined with any one of the nitrogen-free analogues, including the possibility of combining a single amino acid with one of its own nitrogen-free analogues.

TABLE I

Essential and Semi-Essential Amino Acids and Their Corresponding Keto- and Hydroxy-Analogues (Nitrogen-Free Analogues)

I. Essential Amino Acids (EAA)

| Neutral amino acids | Keto-analogues | Hydroxy-analogues |
|---|---|---|
| L-threonine | IE | IE |
| L-valine | α-ketoisovaleric acid | PIE |
| L-leucine | α-ketoisocaproic acid | PIE |
| L-isoleucine | (R,S)-α-keto-β-methylvaleric acid | PIE |
| L-methionine | α-keto-γ-methiolbutyric acid | (D,L)-α-hydroxy-γ-methiolbutyric acid |
| L-phenylalanine | phenylpyruvic acid | L-phenyllactic acid |
| L-tryptophan | Indolepyruvic acid | Indolelactic acid |

| Basic amino acids | Keto-analogues | Hydroxy-analogues |
|---|---|---|
| L-lysine | IE | IE |
| L-histidine | Imidazolepyruvic acid | Imidazolelactic acid |

II. Semi-Essential Amino Acids

| Neutral amino acids | Keto-analogues | Hydroxy-analogues |
|---|---|---|
| L-tyrosine | p-hydroxyphenylpyruvic acid | L-p-hydroxyphenyllactic acid |
| L-cystine | ββ'-dithiodipyruvic acid | L-ββ'-dithiodilactic acid |
| L-cysteine | β-mercaptopyruvic acid | L-β-mercaptolactic acid |

| Basic amino acids | Keto-analogues | Hydroxy-analogues |
|---|---|---|
| L-arginine | NNF | NNF |
| L-ornithine | NNF | NNF |

IE = ineffective as amino acid precursor
PIE = probably ineffective as amino acid precursor
NNF = not nitrogen-free and PIE Consequently there are over 200 compounds in all which may be formed according to the present invention, even excluding possible combinations with the analogues which may be ineffective as essential amino acid precursors. Not all of the possible combinations have been investigated, but I have investigated a sufficient number of them to be reasonably certain that as a class these novel compounds of the present invention have advantages over the corresponding essential and semi-essential amino acids per se and over the corresponding nitrogen-free analogues thereof, whether the analogues are used as their sodium or calcium salts or as free acids.

Examples of novel compounds of the present invention which have been investigated include those set forth in Table II, with their solubility and taste characteristics. For comparison purposes, the solubility of the least soluble of the two essential or semi-essential amino acids to which the mixed salt corresponds has been set forth in the third column of the table followed by the factor of increased solubility in the fourth column. In some cases, where the two corresponding amino acids are close in solubility, the solubilities of both have been included in the table.

In general, the novel compounds of the present invention are far more palatable than the corresponding essential or semi-essential amino acids per se or the corresponding nitrogen-free analogues. Thus, the compounds of the invention which have been tested are generally either tasteless or have a slightly sweet taste that is quite pleasant. Moreover, the compounds of the invention, as a class, are much more soluble than the corresponding essential or semi-essential amino acids and some nitrogen-free analogues. Most notably, the highly insoluble semi-essential amino acid L-tyrosine becomes readily soluble when combined with the keto-analogue of leucine, for example.

ordinate and moles of amino acid added per mole of nitrogen free analogue as the abscissa) obtained when adding the free base of the amino acid to the acid analogue has an inflection point which appears to coincide with the point at which equimolar quantities of the free base and acid analogue have been combined. The inflection point also appears to correspond, at least approximately, to the isoelectric point or IP of the solution formed by the mixed salt. Therefore, this inflection point will be referred to hereinafter for convenience as the "isoelectric point" or "IP". The accompanying drawing illustrates the pH curve for the titration of alpha-ketoisocaproic acid with lysine free base. As seen in the drawing the IP is the point where the pH changes the most with the smallest addition of acid.

Titration of the acid analogue with the free base of the amino acid to the isoelectric point is preferred since this appears to yield compounds of the present invention having the best taste and probably the greatest solubility. It is believed that optimum taste is achieved at this point since the free base and acid analogue should have combined completely (in equimolar quantities), so that there should be no excess of either the free base or acid analogue to produce any unpleasant taste from such excess. Titration to the isoelectric point is also advantageous since it is often difficult to insure equimo-

TABLE II

| | Solubilities and Taste Characteristics of Examples of Prepared Mixed Salts | | | |
|---|---|---|---|---|
| Mixed Salt | Solubility* of Mixed Salt | Solubility* of Least Soluble** Amino Acid | Approximate Increase in Solubility | Taste Characterization |
| L-lysine alpha-ketoisovalerate | 1.2 M | Valine: 0.71 M | 2 × | Pleasant |
| L-lysine (R,S) alpha-keto-beta-methylvalerate | 2.1 M | Isoleucine: 0.31 M | 7 × | Pleasantly sweet |
| L-lysine alpha-keto-isocaproate | 1.16 M | Leucine: 0.18 M | 6 × | Faintly sweetish |
| L-lysine (D,L)-alpha-hydroxy-gamma-methiol-butyrate | >2 M | Methionine: 0.23 M# | >8 × | Unpleasant |
| L-lysine(L)-phenyl-lactate | 0.5 M | Phenylalanine: 0.18 M | 3 × | Almost tasteless |
| L-lysine phenyl-pyruvate | 0.84 M | Phenylalanine: 0.18 M | 5 × | Almost tasteless |
| L-tyrosine (R,S)-alpha-keto-beta-methylvalerate | 0.33 M | Tyrosine: 0.0025 M | 100 × | Fleeting vinegary taste |
| Histidine (R,S)-alpha-keto-beta-methylvalerate | 0.65 M | Isoleucine: 0.31 M Histidine: 0.27 M | 2 × | Bitter-sweet (like aspirin); no aftertaste |
| Histidine alpha-keto isocaproate | 0.68 M | Leucine: 0.18 M Histidine: 0.27 M | 4 × | Tangy; no aftertaste |
| Tryptophan alpha-keto isocaproate | 0.059 M | Tryptophan: 0.056 M Leucine: 0.18 M | None | Bitter; no aftertaste (unlike tryptophan) |
| Threonine (R,S)-alpha-keto-beta-methylvalerate | >1 M | Isoleucine: 0.31 M | >3 × | Pleasant, faintly sweet taste; no aftertaste |

*at 25° C. expressed in moles of salt per liter of water
**Solubility of least soluble of the two corresponding amino acids is taken from Merck Index (9th Edition)
Value given is for D,L-methionine, solubility of L-methionine is not stated In general, the techniques for preparing the novel compounds of the present invention are relatively simple and straightforward. In the case of the basic essential amino acids, approximately equimolar quantities of the free base of the selected amino acid and the free acid of the selected nitrogen-free analogue are suspended or dissolved in an amount of water which is more than sufficient to dissolve the desired salt which is the reaction product of the free base and the free acid. Stirring and, if necessary, gentle warming may be used for the dissolution.

In preparing the salts of the basic amino acids, it has been found that the titration curve (with pH as the lar quantities of reactants when working with volatile liquids (acid analogues) and incompletely dried solids (free bases).

The resulting solution of product is then evaporated until a precipitate begins to appear. The product is obtained by maintaining the solution at about 4° C. over night, with or without the addition of alcohol or acetone, followed by filtration and drying. Instead of precipitation, the product may advantageously be recovered by lyophilization or spray drying to avoid distortion of the molar ratio occurring when an organic solvent is used. Alternatively, the solution may be used as is or suitably concentrated or diluted for use by intravenous injection.

Where the essential or semi-essential amino acid is a neutral amino acid, it is necessary to use a substantial excess of the free acid of the nitrogen-free analogue as compared to the amino acid. The excess free acid is dissolved and removed by alcohol used in the precipitation step. Otherwise, the general technique is the same.

In both cases, the resulting reaction product is a dry white powder which is not particularly hygroscopic. The reaction product does not appear to contain any excess free acid or free base, since the presence of free acids (which are liquids) would prevent the formation of a dry powder, and the presence of free base would make the removal of water almost impossible.

The salts formed by reaction of neutral amino acids and nitrogen-free analogues are somewhat acidic, yielding a pH of about 3 in water. Salts formed from L-lysine or L-arginine and various nitrogen-free analogues yield a pH of approximately 5 in water. L-histidine salts yield a pH of about 4 to 4.5 in water.

The stability of the novel compounds of the present invention appears to be comparable to the stability of the corresponding sodium or calcium salts of the nitrogen-free analogues. That is, they are generally stable in the dry state at room temperature. The salts decompose slowly in solution at room temperature, rapidly in boiling solution and not at all in frozen solution.

The novel compounds of the present invention appear certain to have the same physiological and therapeutic effects as the essential or semi-essential amino acids and nitrogen-free analogues to which they correspond. It is also unlikely that the compounds would have any other effects on the human body than the effects of the corresponding amino acids and nitrogen-free analogues. Hence, the choice of the particular salts of the present invention to be made and used in treatment of renal and hepatic disorders will be based on essentially the same criteria as were previously used in selecting essential or semi-essential amino acids per se or the nitrogen-free analogues per se. However, palatability and solubility characteristics will no longer be limiting factors.

The novel compounds of the present invention would generally not be used individually unless there were an indication that the patient was deficient in only two of the essential or semi-essential amino acids. However, patients with kidney or liver disease who are on restricted protein intakes are likely to benefit from mixtures of compounds of the present invention which correspond to more than two of the essential or semi-essential amino acids. In general, the choice of the salts to be made and used in the treatment of patients with nitrogen wasting disorders will be based upon the degree of reduction of the concentrations of individual essential and semi-essential amino acids observed in the plasma or muscle cells of the patients.

Where it is desired to administer salts of the present invention to provide more than two precursors of essential or semi-essential amino acids, this may be done in several different ways. For example, separate salts may be made individually, each salt corresponding to two of the essential or semi-essential amino acids for which precursors are desired in the therapeutic composition. The separate salts would then be mixed together either in dry powder form or solution form for oral or parenteral administration, respectively.

Alternatively, all of the essential and/or semi-essential amino acids and nitrogen-free analogues to be used may be mixed together in the same aqueous medium to form a mixture of all of the possible combinations of these amino acids with these particular analogues. In this procedure, the reactants which are to be present in the form of nitrogen-free analogues are obtained as the free acids of the analogues and mixed with a convenient volume of water (most of these are liquids which are miscible in water or solids of reasonably high solubility in water). To this solution are then added the essential and/or semi-essential amino acids which are to make up the cations of the salts (the basic amino acids are added as free bases, while the neutral amino acids are added as such). As the basic amino acids are added, the pH of the mixture rises, and at a pH of approximately 4 to 5, the addition of basic amino acids is stopped. Water is then removed by evaporation and the residue is redissolved in ethanol and then dried in air.

In the case of a highly insoluble essential or semi-essential amino acid, such as L-tyrosine, it may be advantageous to simply add the amino acid as such to the dry mixture of salts after they have been prepared. In such a case, the tyrosine or other amino acid added dry would not enter into a chemical reaction or form a novel chemical entity. Thus, the reaction products of the present invention require an aqueous medium for formation.

Except where a dry amino acid such as L-tyrosine is to be used in the mixture, all of the compounds of the present invention alone or in combination can be given intravenously in aqueous solution. As previously indicated, the pH of solutions of novel compounds of the invention using basic amino acids to titrate the acid analogues is approximately 5 if titrated to the isoelectric point. Thus, for example, at the isoelectric point the pH of lysine salts is approximately 5.1 to 5.3 and the pH of histidine alpha-keto isovalerate is approximately 4.3. Since the salts of the present invention are so strongly associated that they are very poor conductors, it is difficult to obtain pH measurements of dilute solutions. However, it has been observed that the addition of 10 volumes of water to concentrated solutions of the salts does not appreciably alter the pH.

Although the acidity of solutions of salts of the present invention at a pH of about 5 might be irritating in a peripheral vein, the solutions could be administered via a central vein without causing any irritation. This is important in view of the advantages of high solubility of these salts as this pH. Thus, the high solubility allows administration of the required doses of essential amino acids with a minimal amount of water in subjects who have a limited capacity for excretion of water loads. This would be particularly important in cases of acute renal failure, and important to a lesser extent in patients with chronic hepatic disorders or chronic renal failure.

There are a number of factors to be considered in determining whether a given essential amino acid or semi-essential amino acid is to be reacted in the form of the amino acid per se or the hydroxy or keto analogue thereof in order to form novel compounds of the present invention. First, as indicated in Table I, a number of the analogues are either ineffective or probably ineffective, and in such cases it is probably preferable to use the amino acid per se. Second, my issued patents cited above indicate that the branched-chain keto acids in particular may exert anabolic effects not shared by the branched-chain amino acids per se. Although there is some controversy regarding such effects, the "carry over" phenomenon which has been repeatedly observed following administration of branched-chain keto acids has not been observed following administration of the branched-chain amino acids per se. Therefore, in the case of valine, leucine nd isoleucine, it may be preferable to use the keto analogues thereof in forming compounds of the present invention.

A third criterion might be price if other factors are not controlling. Thus, for example, the hydroxy analogue of methionine is much less expensive than methionine per se. Fourth, as indicated in Table II, the novel compounds of the present invention may differ significantly in taste and solubility, so that these factors may be determinative depending upon whether the compound is to be used in oral or intravenous administration, respectively.

The invention will now be illustrated with reference to the following specific, non-limiting examples:

EXAMPLE I

The plasma or muscle cells of uremic patients are observed to be deficient in the essential amino acids valine, leucine, isoleucine, histidine, threonine and lysine and the semi-essential acid tyrosine. They do not appear to be deficient in other essential amino acids, namely phenylalanine, methionine and tryptophan. The deficiency in valine is greater than that of any other of the amino acids. Therefore, a mixture of salts according to the present invention is prepared by reacting the following compounds in aqueous medium in the following relative molar proportions: 4 parts alpha-keto-isovaleric acid, 1 part alpha-keto isocaproic acid, 1 part alpha-keto-beta-methylvaleric acid, 1 part histidine, 2 parts threonine, and 2 parts lysine, according to the following procedure:

The free keto acids (which are liquids) are weighed out in the desired portions as indicated above and mixed together. One volume of this mixture is added to one volume of water. The portion of threonine is then added as the dry amino acid. Lysine free base is added to a nearly saturated solution of histidine free base in a molar ratio of 2:1. This basic solution is then used to titrate the former solution until the total solution has a pH of approximately 4.5. Water is removed from this total solution by evaporation at 40° C. until the solution begins to look cloudy. A small volume of ethanol is added and the mixture placed in the refrigerator at 4° C. over night. Five volumes of ethanol are then added and the product is collected by filtration and drying in air. After the product is completely dry, it is ground with one mole of tyrosine to yield a composition containing precursors of six essential amino acids in the form of compounds of the present invention and the semi-essential amino acid tyrosine per se.

It is observed that the above reaction products mix, without the subsequent addition of tyrosine, is clearly a mixture of new compounds, rather than simply a physical admixture of the essential or semi-essential amino acids and nitrogen-free analogues. Thus, when the same ingredients are mixed together without the addition of water and its subsequent removal, an offensive and malodorous slush is formed. The reason for this is that both lysine free base and the free keto analogues are extremely malodorous and offensive, and in the absence of water they do not react completely to form the novel compounds of the present invention.

EXAMPLE II

Another composition which may be used in the treatment of renal failure is prepared by mixing in a dry state the following novel compounds of the present invention plus amino acids per se in the following relative molar proportions: 1 part lysine alpha-keto-isovalerate, 1 part histidine alpha-keto-isovalerate, 1 part lysine alpha-keto-isocaproate, 1 part lysine alpha-keto-beta-methylvalerate, 1 part threonine and 1 part tyrosine. Each of the lysine and histidine mixed salts is prepared by titrating the alpha-keto analogue in water with lysine or histidine free base, respectively until the respective isoelectric point is reached. Each compound is then recovered in the dry form by precipitation and drying as described above. Since threonine and tyrosine do not taste particularly bad, they are used per se by mixing and grinding with the dry lysine and histidine salts. An advantage of this composition over that of Example I is that the novel compounds of the invention may be prepared and stored in dry form and then combined just before administration. This mixture may be administered to patients suffering from renal failure in dosages of about 10 to 15 grams of the mixture per day.

EXAMPLE III

The novel compounds of the present invention may be advantageously used in the treatment of hepatic disorders, particularly portal-systemic encephalopathy, in combination with ornithine salts of branched-chain keto acid which are disclosed in my U.S. Pat. No. 4,228,099. A suitable mixture of this type would include one mole each of the three ornithine salts of branched-chain keto acids, one mole each of the three lysine salts of branched-chain keto acids formed according to the present invention, and one or two moles of threonine. All of these compounds are reasonably pleasant in taste and may be mixed together in dry form.

Additional compositions comprising mixtures of salts according to the present invention for treatment of renal and hepatic disorders and other nitrogen wasting diseases will occur to those skilled in the art in view of this disclosure. For example, a mixture of compounds representing all nine of the essential amino acids in either the amino acid form or the nitrogen-free analogue form could be made as above. Such a mixture of novel compounds would be as effective as a simple mixture of the nine essential amino acids per se, and would have the advantage of being much more palatable, and therefore acceptable for oral therapeutic administration.

For the treatment of protein wasting and malnutrition, a composition may be made using compounds of the present invention which collectively contain all of the essential amino acids plus arginine, except that methionine (whose salts are unpleasant tasting) would preferably be used in capsule or tablet form in order to mask its taste.

From the increased solubility and change in taste which occur when combining the essential or semi-essential amino acids and nitrogen-free analogues thereof according to the present invention, it appears clear that new chemical entities are formed. The fact that the titration curve from adding free base to acid analogues has an inflection point coinciding with equimolar addition is also good evidence of the creation of new chemical entities.

Although I do not wish to be bound by any particular theory, I believe that the new chemical entity may be present in solution or in the dry powder in any of all of three different forms, including (1) a mixed salt wherein the amino acid is the cation and the keto acid or hydroxy acid analogue is the anion; (2) a carbinolamine; and (3) the Schiff base which is formed by spontaneous and reversible dehydration of the carbinolamine. These three forms should be in equilibrium, of which the relative proportions are unknown, but which may be represented by the formulas shown below, wherein $R_2$ is the hydrocarbon skeleton of the essential or semi-essential amino acid and $R_1$ is the hydrocarbon skeleton of the analogue of an essential or semi-essential amino acid.

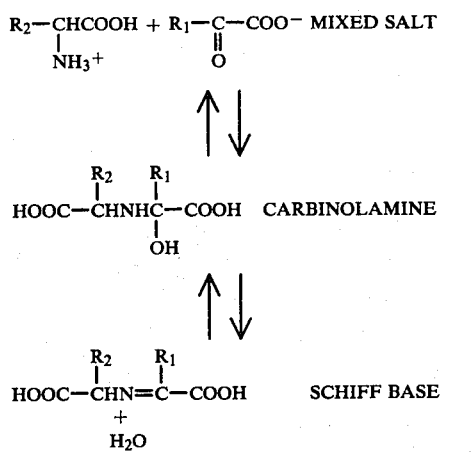

The present invention may be embodied in other specific forms without departing from the spirit or essential attributes thereof and, accordingly, reference should be made to the appended claims, rather than to the foregoing specification as indicating the scope of the invention.

I claim:

1. A composition useful for providing essential and semi-essential amino acids to the body for the treatment of renal disease in humans, comprising the reaction product of the following compounds in approximately the indicated molar proportions:
   4 parts alpha-keto-isovaleric acid
   1 part alpha-ketoisocaproic acid
   1 part alpha-keto-beta-methylvaleric acid
   1 part histidine
   2 part threonine
   2 part lysine
said reaction product formed in aqueous medium followed by removal of water.

2. A composition according to claim 1 wherein the dry powder reaction product has added thereto approximately 1 part tyrosine.

3. A method of treating renal disease in humans comprising administering orally in effective dosage the composition of claim 2.

4. A composition useful for providing essential and semi-essential amino acids to the body for treatment of renal disease in humans, comprising a dry mixture of the following compounds in approximately the indicated molar proportions:
   1 part lysine alpha-keto-isovalerate
   1 part histidine alpha-keto-isovalerate
   1 part lysine alpha-keto-isocaproate
   1 part lysine alpha-keto-beta-methylvalerate
   1 part threonine
   1 part tyrosine
wherein said compounds were formed in aqueous medium.

5. A composition useful for providing essential and semi-essential amino acids to the body for treatment of hepatic disease in humans, comprising a dry mixture of the following compounds in approximately the indicated molar proportions:
   1 part each of the three lysine salts of branched-chain keto acid analogues
   1 part each of the three ornithine salts of branched-chain keto acid analogues
   1 to 2 parts of threonine
wherein said compounds were formed in aqueous medium.

6. A composition useful for providing essential and semi-essential amino acids to the body for treatment of protein wasting and malnutrition, comprising a mixture of two or more salts which are the reaction products of essential or semi-essential amino acids with nitrogen-free analogues of essential or semi-essential amino acids, said reaction products formed in aqueous medium and including salts of arginine and eight essential amino acids except methionine, and methionine is present per se in capsule or tablet form.

* * * * *